US006956149B1

(12) United States Patent
Richards et al.

(10) Patent No.: US 6,956,149 B1
(45) Date of Patent: Oct. 18, 2005

(54) METHOD OF CONVEYING BNYVV RESISTANCE TO SUGAR BEET PLANTS

(75) Inventors: Kenneth Richards, Pfulgriesheim (FR); Gérard Jonard, Strasbourg (FR); Hubert Guilley, Berstett (FR); Cornelis Maria Petrus Van Dun, Roosendaal (NL)

(73) Assignee: SES Europe N.V./S.A. (BE)

( * ) Notice: Subject to any disclaimer, the term of this patent is extended or adjusted under 35 U.S.C. 154(b) by 0 days.

(21) Appl. No.: 09/889,938

(22) PCT Filed: Jan. 26, 2000

(86) PCT No.: PCT/EP00/00609

§ 371 (c)(1),
(2), (4) Date: Dec. 11, 2001

(87) PCT Pub. No.: WO00/44915

PCT Pub. Date: Aug. 3, 2000

(30) Foreign Application Priority Data

Jan. 27, 1999 (EP) .............................. 99200236

(51) Int. Cl.[7] .................. C12N 15/82; C12N 15/90; C12N 5/10; A01H 5/00; A01H 5/10
(52) U.S. Cl. ................. 800/301; 435/320.1; 435/419; 435/468; 800/280; 800/298
(58) Field of Search ..................... 435/410, 419, 435/468, 320.1; 800/278, 279, 280, 295, 298, 301

(56) References Cited

FOREIGN PATENT DOCUMENTS

| WO | WO 90/08826 | 8/1990 | ........... C12N/15/54 |
|----|-------------|--------|------------------------|
| WO | WO 93/21334 | 10/1993 | ........... C12N/15/82 |
| WO | WO 93/25068 | 12/1993 | ............ A01H/4/00 |
| WO | WO 96/37609 | 11/1996 | ........... C12N/15/52 |

OTHER PUBLICATIONS

Tang et al., Genes Dev., 2003, vol. 17, pp. 49–63.*
Baulcombe, D.C., Plant Cell, 1996, vol. 8, pp. 1833–1844.*
I. Jupin et al., "Pathogenesis of beet necrotic yellow vein virus," Virology, vol. 2, 199: pp. 121–127.
S. Bouzoubaa et al., "Nucleotide Sequence of Beet Necrotic Yellow Vein Virus RNA–1," J. Gen. Virol. (1987), vol. 68, 615–626.

M.F. Clark and D.J. Barbara; *A method for the quantitative analysis of ELISA data*, Journal of Virological Methods, 15 (1987); 213–222.
P.G. Vancanneyt, R. Schmidt, A. O'Connor–Sanchez, L. Willmitzer, M. Rocha–Sosa; *Construction of an introncontaining marker gene; Splicing of the intron in transgenic plants and its use in monitoring early events in Agrobacterium–mediated plant transformation*, MGG © Springer–Verlag 1990; 245–250.
J. Donson, C.M. Kearney, T.H. Turpen, I.A. Khan, G. Kurath, A.M. Turpen, G.E. Jones, W.O. Dawson, and D.J. Lewandowski; *Broad Resistance to Tobamoviruses Is Mediated by a Modified Tobacco Mosaic Virus Replicase Transgene*, MPMI, vol. 6, No. 5, 1993; 635–642.
M. Mannerlof, B–L Lennerfors, P. Tenning; *Reduced titer of BNYVV in transgenic sugar beets expressing the BNYVV coat protein*, Euphytica 90: 1996; 293–299.
J. Kallerhoff, P. Perez, S. Bouzoubaa, S.B. Tahar, J. Perret; *Beet necrotic yellow vein virus coat protein–mediated protection in sugarbeet (Beta vularis L.) protoplasts;* Plant Cell Reports © Springer–Verlag 1990; 224–228.
R.D. Hall et al., *A high efficiency technique for the generation of transgenic sugar beets from stomatal guard cells*, Nature Biotechnology, vol. 14, Sep. 1996; 1133–1138.
F.A. Krens et al.; *The effect of exogenously–applied phytohormones on gene transfer efficiency in sugarbeet (Beta vulgaris L.);* Plant Science 116 (1996); 97–106.
E.W. Myers and w. Miller; *Optimal alignments in linear space:* CABIOS, vol. 4, No. 1 (1988); 11–17.
W.J. Wilbur and D.J. Lipman; *Rapid similarity searches of nucleic acid and protein data banks;* Proc. Natl. Acad. Sci. USA, vol. 80 (1983) 726–730.

* cited by examiner

*Primary Examiner*—Ashwin Mehta
(74) *Attorney, Agent, or Firm*—The Webb Law Firm

(57) ABSTRACT

The present invention relates to a method for conveying resistance to beet necrotic yellow vein virus (BNYVV) to a sugar beet plant, which method comprises the following steps: (a) preparing a DNA fragment consisting of a nucleotide sequence that corresponds to nucleotides 153 to 3258 of the genomic RNA 1 of the beet necrotic yellow vein virus (BNYVV); (b) introducing said DNA fragment, operatively linked to a promoter that is active in sugar beet plants, into a sugar beet plant cell to obtain a transformed sugar beet cell; and (c) regenerating a transgenic sugar beet plant from the transformed sugar beet plant cell.

9 Claims, 7 Drawing Sheets

Southern analysis sugar beet transformant T157-01 (pVDH239)

Probe: GUSi

Conclusion: T157-01 contains 3 inserts

Bioassay rhizomania resistance T157-1

FIG. 4

Probe: Gus
Enzyme SacI

METHOD OF CONVEYING BNYVV RESISTANCE TO SUGAR BEET PLANTS

BACKGROUND OF THE INVENTION

The present invention relates to a method for conveying viral resistance to beet necrotic yellow vein virus (BNYVV) to a sugar beet plant. Furthermore, the invention relates to virus-resistant plants obtained according to this method, as well as to seeds and progeny derived therefrom.

DESCRIPTION OF THE RELATED ART

Plant viruses are a serious problem for many of the major agricultural crops. Thus, BNYVV which is transmitted by the soilborne plasmodiophoromycete fungus *Polymyxa betae*, is the cause of the economically important disease of sugar beet (*Beta vulgaris*), known as rhizomania. This disease was first reported in Italy in the 1950s and has since become a major threat to sugar beet crops in most growing areas in the world.

Under field conditions BNYVV is generally confined to the subterranean portions of the plant. Infected sugar beet roots exhibit an increased proliferation and necrosis of the lateral roots, a decrease in the total mass of the main root and a consequent reduction in sugar yield. Plant death may also follow infection, particularly if the crop is infected early in season. Occasionally, the virus will ascend into the leaves where it can provide invasive vein-associated chlorotic and necrotic lesions.

BNYVV is a type member of the benyvirus family, which are fungus-transmitted, rod-shaped viruses possessing a divided genome composed of two or more components of single-stranded (ss) RNA. Four different plus sense ssRNA species of BNYVV have been identified, which are referred to as RNAs 1 to 4 in decreasing order of size (RNA 1: 6.8 kb; RNA 2: 4.7 kb; RNA 3: 1.8 kb; RNA 4: 1.5 kb). Some Japanese isolates also contain a fifth RNA component (RNA 5: 1.45 kb). All RNAs have been cloned and sequenced. The genetic map of the viral RNAs is shown in FIG. 1.

All five RNAs terminate in 3' poly-A tails, and RNAs 1–4 have cap structures at their 5' termini. RNAs 1 and 2 encode basic host-independent "housekeeping" functions, while the smaller RNAs intervene specifically in the natural infection process, including vector-mediated infection of sugar beet roots, proliferation within the root system and production of rhizomania symptoms. Thus, RNA 1 has been shown to code for viral RNA polymerase activity and RNA 2 encodes the 21-kd viral coat-protein. The 3'-proximal half of RNA 2 carries a group of three successive slightly overlapping viral genes, known as the triple gene block (TGB3), that are closely similar to a cluster of three genes in other rod-shaped plant viruses, and are involved in cell to cell movement of the virus. RNA 3 is associated with massive proliferation of fine rootlets in sugar beet and facilitates the spread of the virus in root tissue, whereas RNA 4 increases the efficiency of transmission of the virus by the fungus.

Fungus-transmitted viruses, such as BNYVV may be retained in resting spores in soil for years once a field becomes infested. As there exist no effective chemical or physical methods for eliminating the virus, neither in the plants nor in the soil, the only option for the sugar beet farmer is the use of genetically resistant cultivars. Several companies have provided a number of tolerant, even partially resistant varieties, by transferring wild type tolerance genes into commercially varieties through breeding. This is, however, a very tedious and time-consuming process, generally taking a long time before useful resistant plants are obtained. In addition, under high disease pressure tolerant or partially resistant plants will develop disease symptoms because the resistance level is too low. Another problem with tolerant or only partially resistant plants lies in the fact that virus populations continue to grow resulting in the possible emergence of a BNYVV strain which may break the resistance/tolerance genes.

The rapid revolution in the areas of plant engineering has led to the development of new strategies to confer genetic resistance to viruses. Resistance to viral diseases through the introduction of portions of viral genome sequences has become a new source of resistance. The viral sequence (construct) is transformed into a plant by combining the use of appropriate cell or tissue culture techniques and a DNA delivery system such as the well known *Agrobacterium tumefaciens* transformation system or the direct DNA transfer mediated by chemicals like polyethylene glycol (PEG).

Known methods of inducing pathogen defense mechanisms in plants are for example described in EP 9687106.0, which relates to a method for inducing resistance to a virus comprising a TGB3 sequence. The publication describes that it was possible to induce BNYVV resistance by a method, which consists of transforming plant cells with a DNA construct corresponding to a fragment of the nucleic acid sequence of the genomic or subgenomic RNA 2 of the BNYVV. The disadvantage of this method is however, that only tolerance is obtained, and not resistance. In tolerant host plants there can still be normal levels of plant virus replication, but the plant shows little or no visible signs of infection, whereas in resistant hosts the virus replication is low or even absent.

In WO 93/25068 viral resistance in plants is induced by plant transformation with a replicase portion (RNA 1) of a plant virus genome. This publication does not refer to sugar beet, nor to BNYVV.

SUMMARY OF THE INVENTION

Sugar beet are known to be recalcitrant species in genetic engineering, complicating successful induction of BNYVV resistance. However, because of the extent and impact of the viral disease of BNYVV there is a major interest to improve the sources of genetic resistance in sugar beet plants.

The object of the present invention is, therefore, to provide means to obtain sugar beet plants, that exhibit resistance to BNYVV. Preferably, they exhibit total resistance or immunity, by combining different approaches and by using methods which do not allow the virus to replicate.

This is achieved by the invention by providing a method for conveying resistance to beet necrotic yellow vein virus (BNYVV) to a sugar beet plant, comprising the following steps:

(a) preparing a DNA fragment of at least 15 nucleotides in a sequence that is essentially homologous to the corresponding nucleotide sequence of the genomic RNA 1 of the beet necrotic yellow vein virus (BNYVV), (b) introducing said DNA fragment, operately linked to a promotor that is active in sugar beet plants, into a sugar beet plant cell to obtain a transformed sugar beet cell; and (c) regenerating a transgenic sugar beet plant from the transformed sugar beet plant cell.

Thus, a sugar beet plant is obtained which exhibits a durable resistance and in which the virus does not replicate.

This is a unique aspect of the transformant of the invention and has not been disclosed before.

According to the invention the essential sequence homology of the fragment is a homology of at least 70%, preferably at least 80%, more preferably at least 90%, most preferably at least 95%.

The homology or "degree of similarity" is used to denote nucleotide sequences which when aligned have similar (identical or conservatively replaced) nucleotides in like positions or regions. For example, two nucleotide sequences with at least 85% homology to each other have at least 85% homologous (identical or conservatively replaced nucleotides) in a like position when aligned optimally allowing for up to 3 gaps, with the provision that in respect of the gaps a total of not more than 15 amino acid residues is affected. The degree of similarity may be determined using methods well known in the art (see, for example, Wilbur, W. J. and Lipman, D. J. "Rapid Similarity Searches of Nucleic Acid and Protein Data Banks." Proceedings of the National Academy of Sciences USA 80,726–730 (1983) and Myers E. and Miller W. "Optimal Alignments in Linear Space". Comput. Appl. Biosci. 4:11–17 (1988)). One programme which may be used in determining the degree of similarity is the MegAlign Lipman-Pearson one pair method (using default parameters) which can be obtained from DNAstar Inc, 1228, Selfpark Street, Madison, Wis., 53715, USA as part of the Lasergene system. The test for homology of the sequence is based on the percent identity which is calculated by Fast DB based on the following parameters: mismatch penalty 1.0, gap penalty (1.00), gap size penalty 0.33 and joining penalty 30.0.

BRIEF DESCRIPTION OF THE DRAWINGS

FIG. 4 is a diagram of the individual ELISA values of the root extracts of various populations of sugar beet plants;

DETAILED DESCRIPTION OF THE PREFERRED EMBODIMENTS

Figure 1:
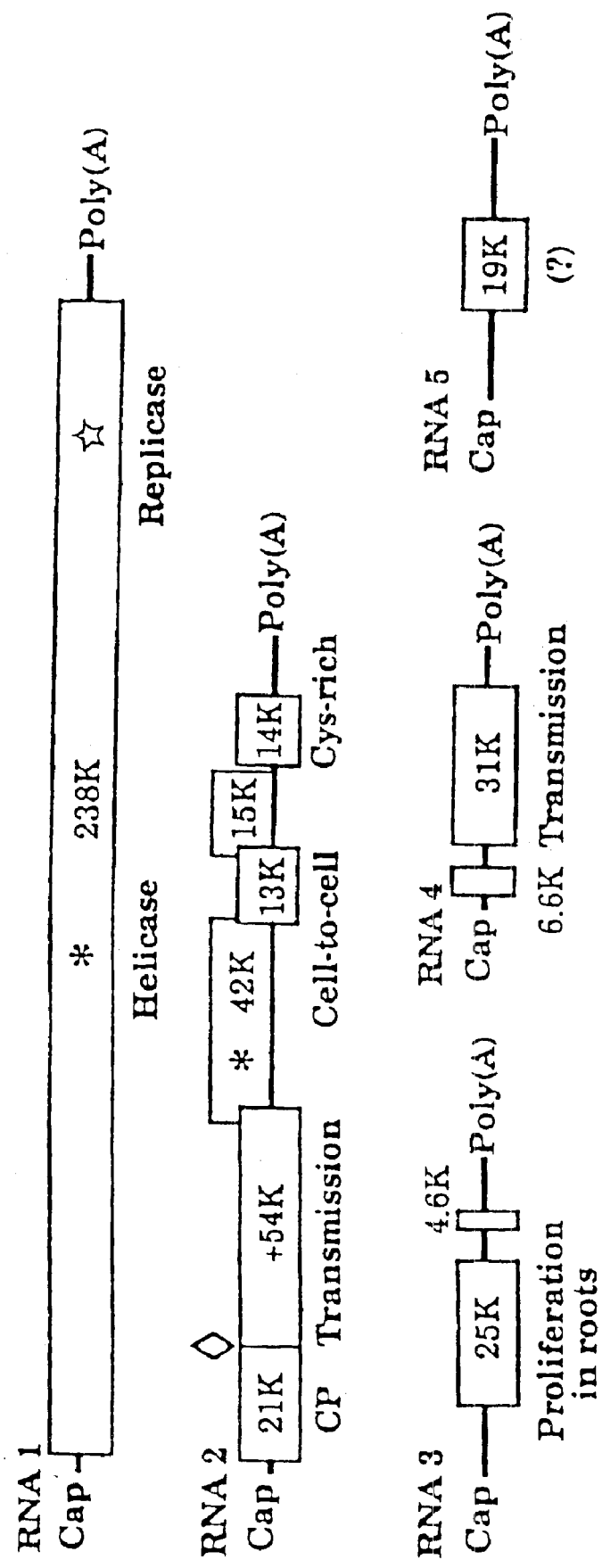
FIG. 1 is a diagrammatic representation of the genomic organization of Beet Necrotic Yellow Vein Virus.

Preferred embodiments of the invention use various fragments having nucleic acid sequences that correspond with the homology indicated or completely to nucleotides 153 to 3258, 169 to 539, 1226 to 1683, 2754 to 3192 or to all of the 6746 nucleotides of RNA 1.

The present invention also includes DNA which hybridises to the DNA of the present invention and which codes for RNA1. Preferably, such hybridisation occurs at, or between, low and high stringency conditions. In general terms, low stringency conditions can be defined as 3×SCC at about ambient temperature to about 65° C., and high stringency conditions as 0.1×SSC at about 65° C. SSC is the name of a buffer of 0.15 M NaCl, 0.015 M trisodium citrate. 3×SSC is three time as strong as SSC and so on.

The fragment can be introduced into a regenerable plant cell by means of a DNA vector harboring the fragment and transcription and translation regulatory sequences operably linked therewith using standard plant transformation methods such as Agrobacterium-mediated transformation of cells embedded in plant tissues such as cotyledons (Krens et al., Plant Science 116: 97–106; 1996) or polyethylene glycol-mediated DNA uptake of single cells like the guard cell protoplasts (Hall et al., Nature Biotechnology 14: 1133–1138; 1996). The DNA vector harboring the fragment is also part of the present invention.

The use of constructs constructed such that the gene sequence inhibits or promotes gene expression is quite well understood. A complete gene sequence, under the control of a promoter that operates effectively in the plant, will generally overexpress the gene product, leading to an amplification of the effect of the protein so produced. Sometimes the gene product is reduced: this phenomenon is termed "co-suppression". Downregulating this gene can be done by several techniques. It can be done by 'dominant-negative', constructs. These contain the specific DNA binding domain as well as possible dimerisation domains but are transcriptionally inactive. They 'sit' on the promoters of the target genes and thereby prevent the binding of the endogenous protein. Additionally, reduction of the gene product can also be obtained by using such dominant negative mutation, or by reversing the orientation of the gene sequence with respect to the promoter so that it produces a type of gene product called "antisense" messenger RNA.

A DNA construct according to the invention may be an "antisense" construct generating "antisense" RNA or a "sense" construct (encoding at least part of the functional protein) generating "sense" RNA.

"Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith).

"Sense RNA" is an RNA sequence, which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International patent Publication WO91/08299).

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA, RNA or synthetic polynucleotide may be used. The transcriptional initiation region (or promoter) operative in plants may be a constitutive promoter (such as the 35S cauliflower mosaic virus promoter) or an inducible or developmentally regulated promoter, as circumstances require. Suitable DNA sequences for control of expression of the plant expressible genes (including marker genes), such as transcriptional initiation regions, enhancers, leader sequences, non-transcribed leaders and the like, may be derived from any gene that is expressible in a plant cell. Also hybrid promoters combining functional portions of various promoters, or synthetic equivalents thereof can be employed. Apart from constitutive promoters, inducible promoters, or promoters otherwise regulated in their expression pattern, e.g. developmentally or cell-type specific, may be used to control expression of the expressible genes according to the invention. For example, it may be desirable to modify protein activity at certain stages of the plant's development. Use of a constitutive promoter will tend to affect protein levels and functions in all parts of the plant, while use of a tissue-specific promoter allows more selective control of gene expression and affected functions.

Another option under this invention is to use inducible promoters. Promoters are known which are inducible by pathogens, by stress, by chemicals and by environmental signals. The induction of the gene activity by internal or external induction is within the scope of the present invention. Promoters of this type enable the inducibility of the gene activity in a controlled manner, thus the plant can develop normally without any undue influence by the transgene gene. Promoters that are inducible promoters include those described in DE 4446342 (fungus and auxin inducible PRP-1), WO 96/28561 (fungus inducible PRP-1), EP 0 712 273 (nematode inducible), EP 0 330 479 and U.S. Pat. No. 5,510,474 (stress inducible), WO/96/12814 (cold inducible), and Zeneca's alcohol inducible promoter. Other inducible promoters are described in EP 0 494 724, EP 0 619 844, WO 92/19724. Thus the gene product, whether antisense or sense RNA or the peptide, is only produced in the tissue at the time when its action is required.

As mentioned above, the term "inducible promoter" includes promoters which may be induced chemically. The use of a promoter sequence which is controlled by the application of an external chemical stimulus is most especially preferred. The external chemical stimulus is preferably an agriculturally acceptable chemical, the use of which is compatible with agricultural practice and is not detrimental to plants or mammals. The inducible promoter region most preferably comprises an inducible switch promoter system such as, for example, a two component system such as the alcA/alcR gene switch promoter system described in the published International Publication No. WO 93/21334, the ecdysone switch system as described in the International Publication No. WO 96/37609 or the GST promoter as described in published International patent Application Nos. WO 90/08826 and WO 93/031294, the teachings of which are incorporated herein by reference. Such promoter systems are herein referred to as "switch promoters". The switch chemicals used in conjunction with the switch promoters are agriculturally acceptable chemicals making this system particularly useful in the method of the present invention.

The skilled person will be capable of selecting a DNA vector for use in these methods. An example of a suitable vector for the *Agrobacterium*-mediated transformation is pBIN19. Suitable vectors for the PEG-mediated transformation include the pBluescript vector or pIGPD7 (Hall et al., Nature Biotechnology 14: 1133–1138; 1996). Introduction of the fragment into these vectors can be achieved by means of standard molecular biological techniques as for example described in Sambrook et al., "Molecular Cloning, A Laboratory Manual", Cold Spring Harbor Laboratory Press; 1989.

Transformed plants obtained by the method of the present invention show absolute resistance, or immunity, to BNYVV. In contrast, previous attempts to convey resistance to plants to BNYVV (Kallerhof et al., Plant Cell Reports 9: 224–228, 1990; and Mannerlof et al., Euphytica 90: 293–299, 1996) or other viruses, such as to tobacco mosaic virus (TMV) (Donson et al., Mol. Plant-Microbe Interact. 6: 635–642; 1993) by transforming plants with portions of the viral genome were less successful. Inoculated leafs still showed symptoms of infection, thus indicating that the resistance is not absolute. It is therefore surprising that the method of the invention is capable of conveying absolute resistance to BNYVV to sugarbeet plants.

Furthermore the invention relates to a transformed plant cell and a transgenic plant resistant to BNYVV as well as reproducible structures, such as seeds, calluses, buds, embryos, obtained from the transgenic plants and the progeny derived therefrom.

In a preferred embodiment of the invention the resistance described herein can be combined with other types of resistance or tolerance to BNYVV.

The invention will further be illustrated in the following examples and figures, but is not limited thereto.

FIG. 1 shows a diagrammatic representation of the genomic organisation of Beet Necrotic Yellow Vein Virus (based on Jupin et al., Seminars in Virology vol 2.2: 112–129; 1991).

Figure 2A:
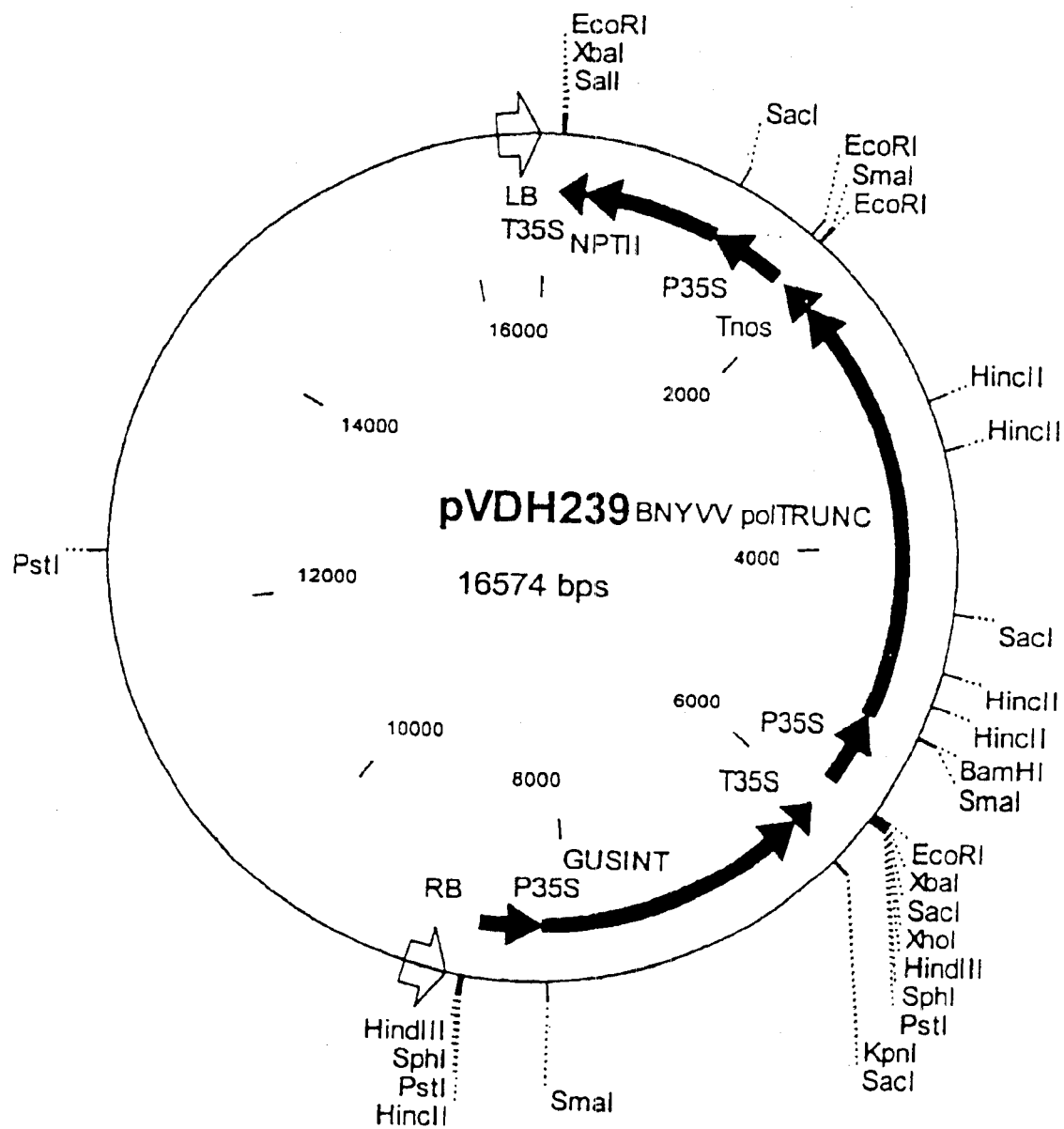
FIG. 2 is a diagram of the physical maps of pVDH239 and pVDH240.
Figure 2B:
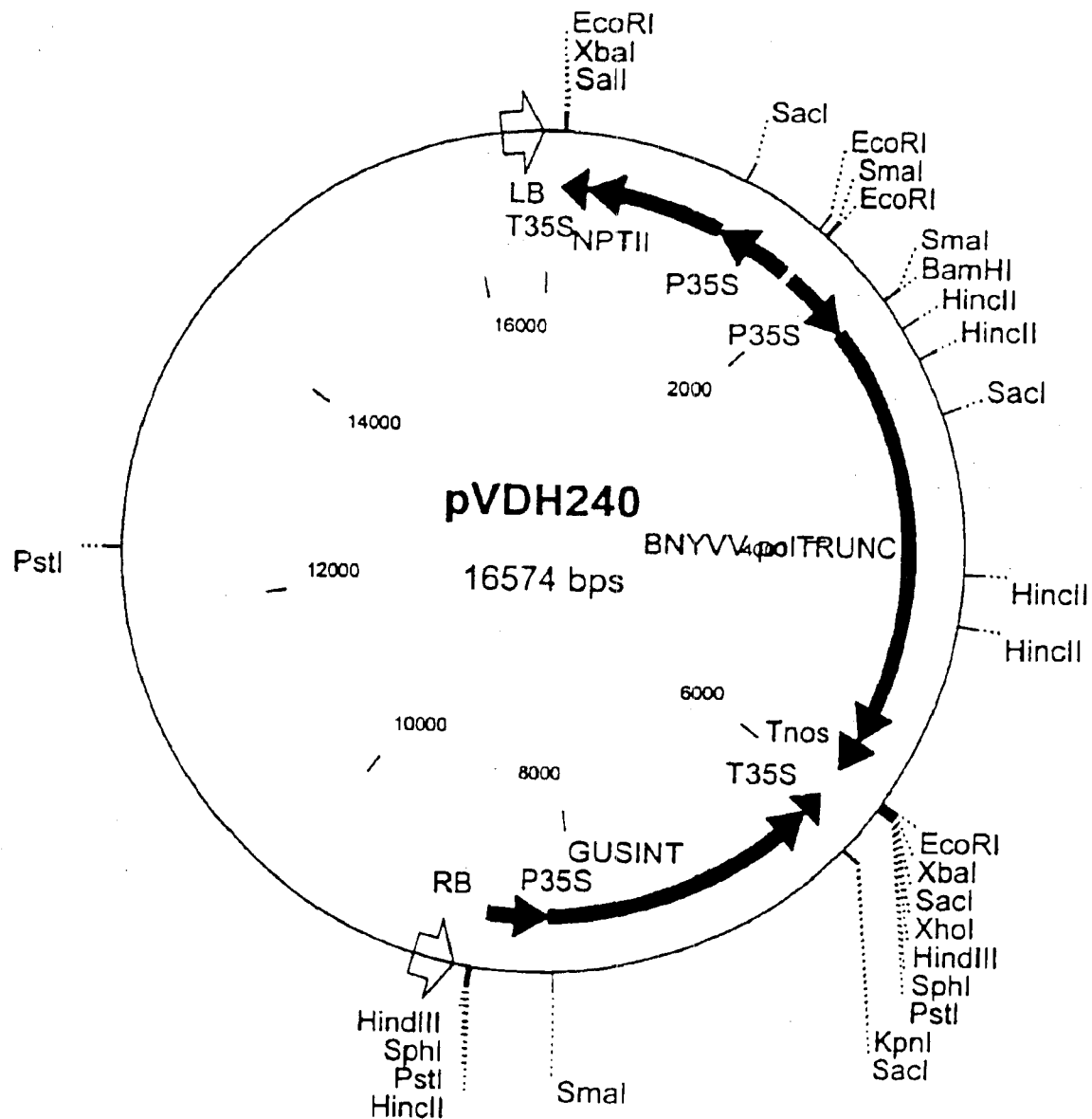

FIG. 2A-B shows the physical maps of pVDH239 and pVDH240. LB=left border, RB=right border, P35S=CaMV 35S promoter, NPTII=neomycin phosphotransferase II, T35S=CaMV 35S polyadenylation signal, GUSINT=beta-glucuronidase gene, BNYVVpolTRUNC=BNYVV cDNA1 fragment, Tnos=nopaline synthase gene derived polyadenylation signal. The positions of the main restriction enzyme recognition sites are indicated.

Figure 3:
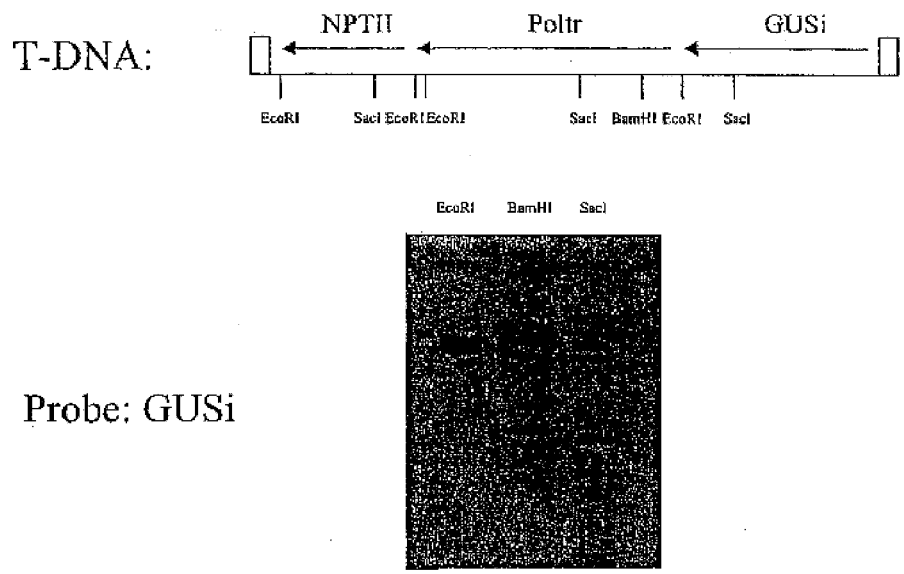
FIG. 3 is a depiction of Southern blot analysis of T-DNA insertions into the genome of the primary sugar beet transformant T157-01.

FIG. 3 shows a Southern blot analysis by which the number of T-DNA insertions integrated into the genome of the primary sugar beet transformant T157-01 has been determined. The outline of the T-DNA structure of the binary vector pVDH239 is shown at the top.

Figure 4:
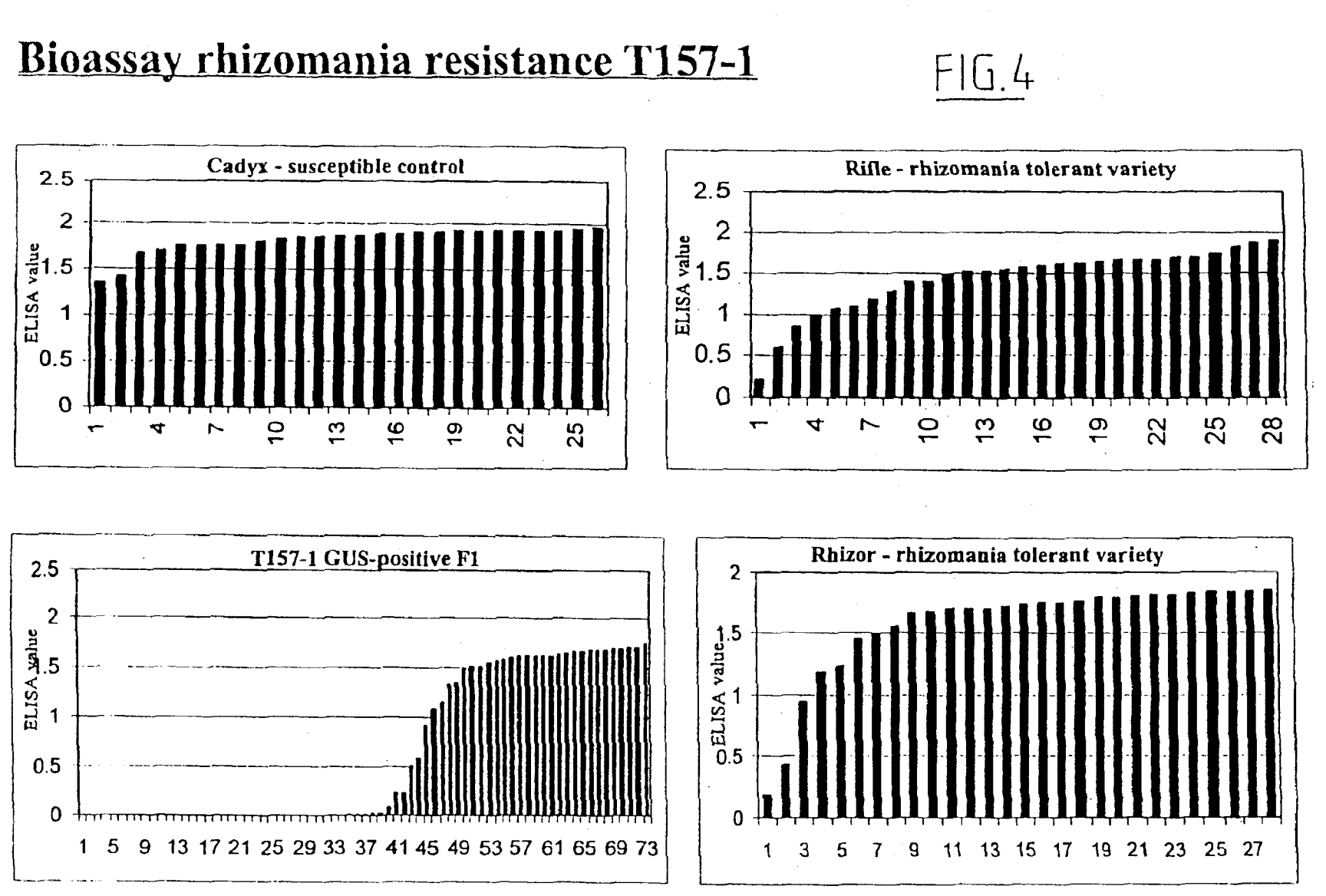

FIG. 4 shows diagrams of the individual ELISA values of the root extracts of sugar beet plants of the populations Cadyx (susceptible control), Rifle (rhizomania tolerant variety), Rhizor (rhizomania tolerant variety) and T157-01 (GUS-positive F1 individuals) after inoculation with BNYVV-infested soil. Each number at the horizontal axis represents an individual plant.

Figure 5A:
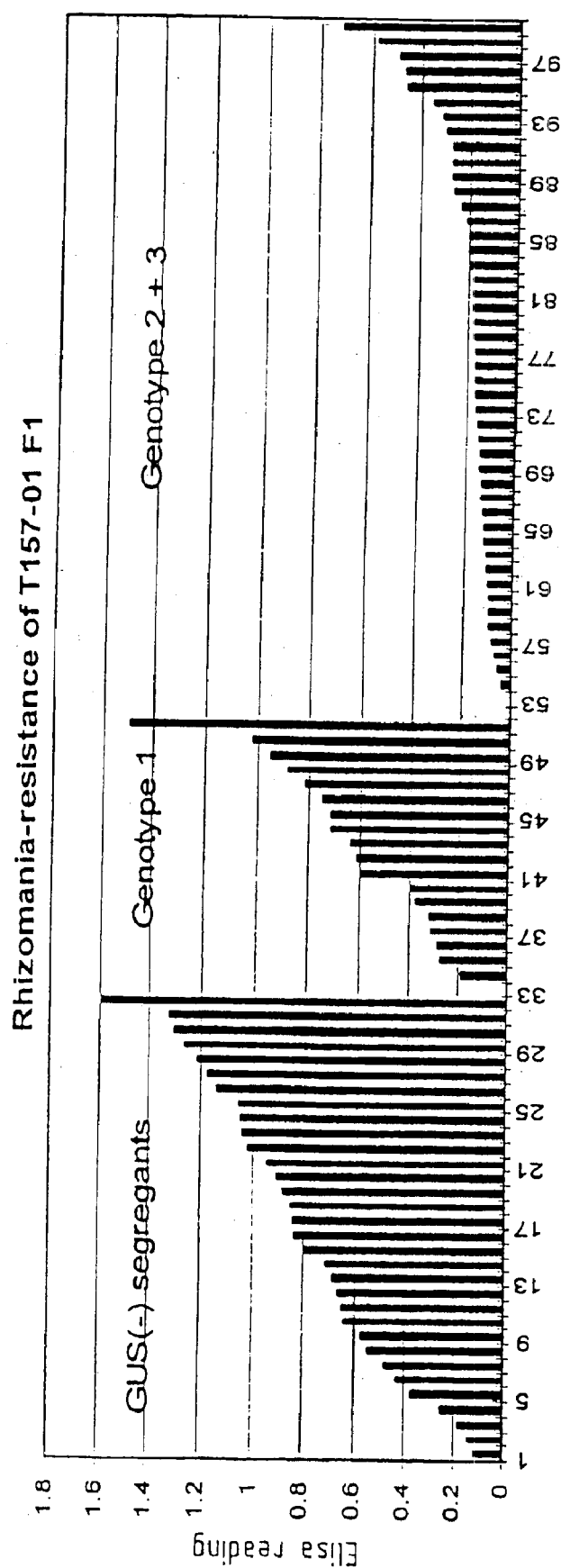
FIG. 5A is a graph of Rhizomania resistance of T157-01 F1.
Figure 5B:
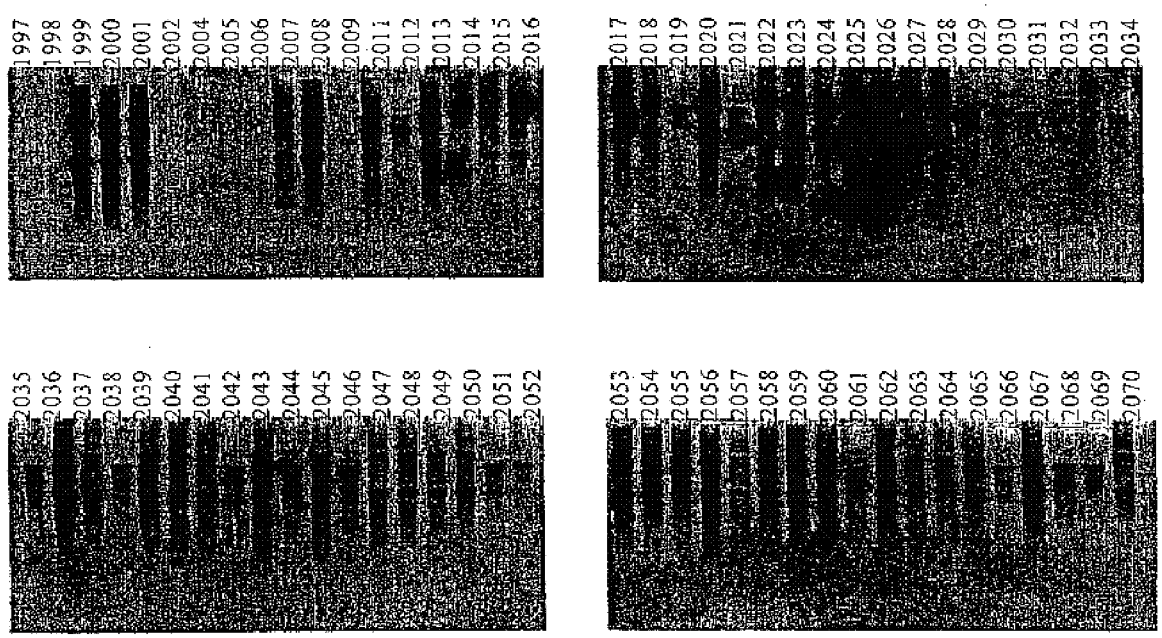
FIG. 5B is a depiction of Southern blot analysis of T-DNA insertions into the genome of the F1 progeny plants of T157-01.

FIG. 5B shows a Southern blot analysis by which the number of T-DNA insertions integrated into the genome of the F1 progeny plants of T157-01 has been determined as well as a diagram of the individual ELISA values of the root extracts of the F1 progeny plants of T157-01) after inoculation with BNYVV-infested soil (FIG. 5A). The numbers on top of the Southern blots represent the lab-codes of the individual F1 progeny plants. The ELISA values indicated by "Genotype 1" in the lower pannel correspond to the indivduals showing a single band in the Southern blot (2012, 2019, 2021, 2029, 2030, 2031, 2034, 2035, 2038, 2042, 2044, 2046, 2051, 2052, 2061, 2066, 2068, 2069), whereas the ELISA values indicated by "Genotype 2+3" in the lower pannel correspond to the individuals showing 2 or 3 bands in the Southern blot (1999, 2000, 2001, 2007, 2008, 2011, 2013, 2014, 2015, 2016, 2017, 2018, 2020, 2022, 2023, 2024, 2025, 2026, 2027, 2028, 2032, 2033, 2036, 2037, 2039, 2040, 2041, 2043, 2045, 2047, 2048, 2049, 2050, 2053, 2054, 2055, 2056, 2057, 2058, 2059, 2060, 2062, 2063, 2064, 2065, 2067, 2070). The ELISA values indicated by "GUS(-)" segregants" in the lower pannel correspond to the individual F1 progeny plants which are GUS-negative (1997, 1998, 2002, 2004, 2005, 2006, 2009, rest not shown).

EXAMPLES

Example 1

Preparation of Contruct with Truncated BNYVV Replicase Sequence

Two primer combinations were used to obtain the cDNA clones of BNYVV for cloning in the transformation vector (Bouzoubaa et al. J. Gen. Virol. 68: 615–626; 1987).
For the 5'-end the primers were
P1: 5'-CGCGGATCCACCATGGCAGATTCGTTC-3' (SEQ ID NO: 1) (containing a BamHI and NcoI restriction site and nucleotides identical to nucleotides 153–168), and
P2: 5'-GACGAATTCAAGTCGTCTTTC-3' (SEQ ID NO: 2) (EcoRI restriction site and nucleotides complementary to nucleotides 288–301).

For the 3'-end the primers were

P3: 5'-GACGAATTCGAAAGATGAGTCTA-3' (SEQ ID NO: 3) (EcoRI site and nucleotides identical to nucleotides 2799–2812), and P4: 5'-CGCAGATCTTTAACTGCTCATCACCAAC-3' (SEQ ID NO: 4) (BglII site and nucleotides complementary to nucleotides 3244–3258 and stop codon).

Before cloning the fragments into the Bluescript vector (Stratagene, La Jolla, Calif., USA) the SalI/HincII/AccI site was replaced by a BglII site. After amplification of BNYVV cDNA using P1 and P2 a DNA fragment was obtained which was digested with BamHI and EcoRI and inserted into the modified, BamHI/EcoRI cleaved pBleuscript vector to yield pKSNBPoll. Subsequently, BNYVV cDNA1 was amplified using P3 and P4. The resulting DNA fragment was cleaved by EcoRI and BglII and inserted into pKSBNPoll cleaved with EcoRI and BglII, yielding pKSNBPpol2.

Thereafter the AccI fragment of BNYVV cDNA1 identical to nucleotides 250–2815 was cloned in AccI cleaved pKSBNPol2. Thus, a pKSBNPoltrunc was obtained which comprised the BNYVV cDNA1 fragment (poltrunc) identical to the nucleotides 153–3258, flanked by a BamHI site at the 5'-end and by a BglII fragment at the 3'-end. The poltrunc fragment was cloned as BamHI-BglII fragment in the BamHI site of pVDH4 such that a functional sense poltrunc fragment was placed behind the CaMV 35S promotor and before the nopaline terminator sequence. The complete construct, carrying the CaMV35S promotor, the poltrunc fragment and nopaline terminator sequence was excised from the plasmid with ClaI and cloned in the binary transformation vector pVDH212 in which the BamHI site was converted into a ClaI site by inserting a molecular linker.

pVDH212 is a pBIN19 derived binary transformation vector, which contains 35S-NPTII (neomycin phosphotransferase under control of the CaMV 35S promotor as a selectable marker gene conferring resistance to kanamycin), as well as 35S-GUSi (gene encoding beta-glucuronidase (Vancanneyt et al., Mol. Gen. Genet. 220: 245–250; 1990). Thus, two different transformation vectors containing the poltrunc construct were obtained: one, pVDH239, with the poltrunc construct in the same transcriptional direction as the NPTII and GUS gene, and another, pVDH240, with the poltrunc construct having an opposite transcriptional direction. The binary transformation vectors pVDH239 and 240

(FIG. 2) were conjugated and transferred to *Agrobacterium tumefaciens* LBA4404 (Phabagen Collection, Utrecht, the Netherlands) resulting in HAT1239 (for pVDH239) and HAT1240 (for pVDH240) strains. HAT1239 and HAT1240 were used for transformation of sugar beet.

Example 2

Transformation of Sugar Beet

Methods for *Agrobacterium*-mediated transformation using binary vectors are well established and known to a person skilled in the art.

To obtain transformed sugar beet plants, O-type B8M5.9 plants were transformed according to Krens et al. (Plant Science 116: 97–106; 1996). Transformation with *Agrobacterium* HAT1239 yielded 8 transformants: T156-03, T156-06, T156-09, T156-10, T156-13, T156-20, T150-30, and T157-01, and with *Agrobacterium* HAT1240 12 transformants were obtained: T183-01, T183-02, T183-06, T183-10, T183-16, T183-19, T183-21, T183-23, T183-26, T184-02, T184-03 and T184-04. The transformants were induced to flowering by vernalisation and used to produce seeds either through self-pollination (selfing or S1 seed) or cross-pollination on male sterile plants (hybrid or F1 seed). The pollination was performed in closed pollen chambers to prevent pollination by sugar beet pollen from a different source.

The F1 seeds were used as starting material to carry out a bioassay for BNYVV resistance. The seedlings were screened initially for GUS activity which indicates the presence of the T-DNA. GUS-negative segregants were used as a negative control in the bioassay. Depending on the total number of T-DNA inserts, the resistance, if present, can segregate within the GUS-positive population. Only T157-01 derived progeny showed BNYVV resistance.

Subsequently, the primary transformant T157-01 was analysed in further detail on Southern blot. Genomic DNA was isolated from leaves, digested seperately with EcoRI, BamHI and SacI and used to prepare a Southern blot which was subsequently probed with GUS. From this experiment it was concluded that the primary transformant contained three T-DNA inserts (FIG. 3).

Example 3

Bioassay

A lateral root bioassay was developed as a single plant test for the selection of rhizomania resistant sugarbeet plants. One-week-old plantlets were transplanted in a standard mixture of 10% rhizomania infected soil and further incubated for 4 weeks. The conditions for infection were optimised and standardised on the level of the infection pressure and the growth of rootlets (only formation of hairy roots). Incubation conditions were: 18.9–19° C. day/night, 70% relative humidity, 10.000 lux white light, pots at 32.5 cm from the lamps.

The amount of virus in the rootlets which was directly correlated with the resistance mechanism in the plant was measured by an ELISA method. The cut-off value for resistant plants was put at an OD-value of 0.2 (Clark et al. J. Virol. Meth. 15: 213–222; 1987). Four weeks after transplantation the lower part of the roots was used for ELISA. The root piece was dried on a filter paper and transferred to a mortar. Extraction buffer was added at a ratio of 10 volume equivalents of the root weight (dilution 1/10). Root juice was extracted by hand crushing. The juice was transferred to 1.5 ml tubes and centrifuged (300 rpm, 10 minutes) the supernatants were kep on ice and assayed. Populations tested were:

| Population | Number of plants | Remarks |
|---|---|---|
| T 157-01 (F1) | 73 | GUS(+) individuals |
| Cadyx F 052 | 26 | sensitive control |
| Rhizor F 202 | 27 | tolerant control |
| Rifle | 28 | tolerant control |

Within the group of T157-01 GUS(+) plants two categories can be observed (FIG. 4). One category displays immunity to BNYVV (ELISA cut-off 0.2) with an average ELISA value of 0.006 which is the background level of the experimental system. The other category shows normal susceptibility with an average ELISA value in the range of the susceptible control.

The infection pressure in this bioassay was high due to the increase of temperature during a part of the infection period. Consequently there was no clear distinction between Cadyx and Rizor/Rifle (FIG. 4). On the other hand, the resistant plants selected in the T 157-01 F1 progeny could be considered as totally resistant independent of the rhizomania infection pressure (FIG. 4). In conclusion, the introduced construct containing the BNYVV cDNA1 fragment resulted in a dramatic negative effect on the multiplication of BNYVV in the lateral roots of the inoculated transgenic sugar beet plants which effectively rendered the plants completely resistant to rhizomania.

In order to explain the segregation of the GUS(+) population in a resistant and a suceptible category the individual plants were analysed in a separate experiment for resistance to BNYVV and simultaneously for the presence of the T-DNAs by Southern analysis using SacI as restriction enzyme and GUS as a probe. The results, as depicted in FIGS. 5A and 5B, point out that the GUS(+) plants within this population which contained a single band on the Southern blot were all susceptible (average ELISA value 0.63), whereas the GUS(+) plants which contained either 2 or 3 bands on the Southern blot were all resistant (average ELISA value: 0.21). The GUS(−) segregants were all susceptible (average ELISA value 0.80). Apparently the resistant phenotype is linked to the presence of the upper and lower band of this particular band pattern obtained on Southern blot, whereas the presence of the middle band is not linked to the resistant phenotype. It is therefore concluded that the segregation of the GUS(+) population into a suseptible and a resistant category can be explained by the fact that one of the T-DNAs which can result in a GUS(+) phenotype does not contribute to the resistance to BNYVV.

What is claimed is:

1. A method for conveying resistance to beet necrotic yellow vein virus (BNYVV) to a sugar beet plant, comprising:

preparing a BNYVV DNA fragment consisting of a nucleotide sequence that corresponds to nucleotides 153 to 3258 of RNA1 of said virus introducing said DNA fragment, operatively linked to a promoter that is active in sugar beet plants, into a sugar beet plant cell to obtain a transformed sugar beet cell; and regenerating a transgenic sugar beet plant from the transformed sugar beet plant cell, said transformed sugar beet plant cell comprising in its genome at least two copies of the DNA fragment, wherein expression of said DNA fragment conveys resistance to BNYVV to said transgenic sugar beet plant.

2. The method of claim 1, wherein the fragment is introduced into the cell by means of a DNA vector comprising said DNA fragment and said promoter operably linked therewith.

3. A transformation vector for conveying resistance to BNYVV to a plant, said vector comprising a DNA fragment consisting of a nucleotide sequence that corresponds to nucleotides 153 to 3258 of RNA1 of said virus, and transcription regulatory sequences operably linked therewith.

4. A transgenic sugar beet plant cell, exhibiting resistance to BNYVV, comprising in its genome at least two copies of a BNYVV DNA fragment consisting of a nucleotide sequence that corresponds to nucleotides 153 to 3258 of RNA1 of said virus.

5. The transgenic plant cell of claim 4, wherein said cell is part of a sugar beet plant that is resistant against BNYVV.

6. A transgenic sugar beet plant exhibiting resistance to BNYVV, comprising plant cells having in their genome at least two copies of a BNYVV DNA fragment consisting of a nucleotide sequence that corresponds to nucleotides 153 to 3258 of RNA1 of said virus, and transcription regulatory sequences operably linked therewith.

7. Progeny of the transgenic sugar beet plant of claim 6, wherein said progeny of the transgenic sugar beet plant exhibit resistance to BNYVV, and further wherein said progeny have in their genome at least two copies of the DNA fragment.

8. Seeds of the transgenic sugar beet plant of claim 6, wherein said seeds of the transgenic sugar beet plant can be grown into a plant that exhibits resistance to BNYVV, and further wherein said seeds have in their genome at least two copies of the DNA fragment.

9. Vegetatively reproducible structures from the transgenic sugar beet plant of claim 6, wherein said vegetatively reproducible structures from the transgenic sugar beet plant can be grown into a plant that exhibits resistance to BNYVV.

* * * * *

UNITED STATES PATENT AND TRADEMARK OFFICE
CERTIFICATE OF CORRECTION

PATENT NO. : 6,956,149 B1
DATED : October 18, 2005
INVENTOR(S) : Richards et al.

It is certified that error appears in the above-identified patent and that said Letters Patent is hereby corrected as shown below:

Column 1,
Line 6, after "BACKGROUND OF THE INVENTION", insert
-- 1.   Field of the Invention --.

Column 2,
Line 39, delete "SUMMARY OF THE INVENTION".
Line 45, insert -- SUMMARY OF THE INVENTION --.

Column 11,
Line 15, "DNA fragment" should read -- cDNA fragment --.
Lines 24-25, "wherein expression of said DNA fragment conveys resistance" should read -- wherein said DNA fragment confers resistance --.

Signed and Sealed this

Second Day of May, 2006

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: primer P1

<400> SEQUENCE: 1
cgcggatcca ccatggcaga ttcgttc                                         27

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer P2

<400> SEQUENCE: 2
gacgaattca agtcgtcttt c                                               21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: primer P3

<400> SEQUENCE: 3
gacgaattcg aaagatgagt cta                                             23

<210> SEQ ID NO 4
<211> LENGTH: 28
<212> TYPE: DNA
<213> ORGANISM: Artificial Sequence
```

```
-continued

<220> FEATURE:
<223> OTHER INFORMATION: Description of Artificial Sequence: primer P4

<400> SEQUENCE: 4
cgcagatctt taactgctca tcaccaac                                              28
```